(12) United States Patent
Iddan

(10) Patent No.: US 7,662,094 B2
(45) Date of Patent: Feb. 16, 2010

(54) OPTICAL HEAD ASSEMBLY WITH DOME, AND DEVICE FOR USE THEREOF

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 10/437,436

(22) Filed: May 14, 2003

(65) Prior Publication Data

US 2003/0227547 A1    Dec. 11, 2003

Related U.S. Application Data

(60) Provisional application No. 60/379,752, filed on May 14, 2002, provisional application No. 60/379,735, filed on May 14, 2002, provisional application No. 60/414,338, filed on Sep. 30, 2002.

(51) Int. Cl.
*A61B 1/06* (2006.01)

(52) U.S. Cl. .................. 600/176; 600/160; 348/340

(58) Field of Classification Search .............. 600/109, 600/129, 160, 179, 175–177; 348/65, 340
See application file for complete search history.

(56) References Cited

U.S. PATENT DOCUMENTS

| | | |
|---|---|---|
| 3,683,890 A | 8/1972 | Beal |
| 3,971,362 A | 7/1976 | Pope et al. |
| 4,178,735 A | 12/1979 | Jackson |
| 4,239,040 A | 12/1980 | Hosya et al. |
| 4,262,632 A | 4/1981 | Hanton et al. |
| 4,278,077 A * | 7/1981 | Mizumoto .................. 600/109 |
| 4,439,197 A | 3/1984 | Honda et al. |
| 4,646,724 A | 3/1987 | Sato et al. |
| 4,689,621 A | 8/1987 | Kleinberg |
| 4,803,992 A | 2/1989 | Lemelson |
| 4,819,620 A | 4/1989 | Okutsu |
| 4,844,076 A | 7/1989 | Lesho et al. |
| 4,936,823 A | 6/1990 | Colvin et al. |
| 4,940,997 A | 7/1990 | Hamlin et al. |
| 5,042,486 A | 8/1991 | Pfeiler et al. |
| 5,081,041 A | 1/1992 | Yafuso et al. |
| 5,109,870 A | 5/1992 | Sliny et al. |
| 5,187,572 A | 2/1993 | Nakamura et al. |
| 5,193,525 A | 3/1993 | Silverstein et al. |
| 5,211,165 A | 5/1993 | Dumoulin et al. |

(Continued)

FOREIGN PATENT DOCUMENTS

DE    2929429    2/1980

(Continued)

OTHER PUBLICATIONS www.rfnorkia.com—NORIKA3, Dec. 24, 2001.

(Continued)

*Primary Examiner*—John P Leubecker
*Assistant Examiner*—Philip R Smith
(74) *Attorney, Agent, or Firm*—Pearl Cohen Zedek Latzer, LLP

(57) ABSTRACT

A device and system including an optical head assembly and a dome, and a method for use thereof. The optical head assembly includes an illumination portion and an imaging portion and is situated behind the dome. The dome may have an optical system integrated therein.

5 Claims, 5 Drawing Sheets

U.S. PATENT DOCUMENTS

| | | | |
|---|---|---|---|
| 5,267,033 | A | 11/1993 | Hoshino |
| 5,279,607 | A | 1/1994 | Schentag et al. |
| 5,330,427 | A | 7/1994 | Weissenburger |
| 5,368,027 | A | 11/1994 | Lubbers et al. |
| 5,395,366 | A | 3/1995 | D'Andrea et al. |
| 5,398,670 | A | 3/1995 | Ortiz et al. |
| 5,429,132 | A | 7/1995 | Guy et al. |
| 5,479,935 | A | 1/1996 | Essen-Moller |
| 5,490,969 | A | 2/1996 | Bewlay et al. |
| 5,495,114 | A | 2/1996 | Adair |
| 5,549,109 | A | 8/1996 | Samson et al. |
| 5,558,640 | A | 9/1996 | Pfeiler et al. |
| 5,604,531 | A * | 2/1997 | Iddan et al. .................. 348/76 |
| 5,697,384 | A | 12/1997 | Miyawaki et al. |
| 5,800,350 | A | 9/1998 | Coppleson et al. |
| 5,819,736 | A | 10/1998 | Avny et al. |
| 5,837,196 | A | 11/1998 | Pinkel et al. |
| 5,892,630 | A * | 4/1999 | Broome .................. 359/834 |
| 5,913,820 | A | 6/1999 | Bladen et al. |
| 5,929,901 | A | 7/1999 | Adair et al. |
| 5,986,693 | A | 11/1999 | Adair et al. |
| 5,993,378 | A * | 11/1999 | Lemelson .................. 600/109 |
| 6,043,839 | A | 3/2000 | Adair et al. |
| 6,099,482 | A | 8/2000 | Brune et al. |
| 6,149,581 | A | 11/2000 | Klingenstein |
| 6,174,291 | B1 | 1/2001 | McMahon |
| 6,228,048 | B1 | 5/2001 | Robbins |
| 6,233,476 | B1 | 5/2001 | Strommer et al. |
| 6,240,312 | B1 | 5/2001 | Alfano et al. |
| 6,285,897 | B1 | 9/2001 | Kilcoyne et al. |
| 6,324,418 | B1 | 11/2001 | Crowley et al. |
| 6,369,812 | B1 | 4/2002 | Lyriboz et al. |
| 6,395,562 | B1 | 5/2002 | Hammock et al. |
| 6,428,470 | B1 * | 8/2002 | Thompson .................. 600/173 |
| 6,475,145 | B1 | 11/2002 | Baylor |
| 6,488,694 | B1 | 12/2002 | Lau et al. |
| 6,632,175 | B1 | 10/2003 | Marshall |
| 6,692,430 | B2 | 2/2004 | Adler |
| 6,836,377 | B1 | 12/2004 | Kislev et al. |
| 7,009,634 | B2 | 3/2006 | Iddan et al. |
| 7,170,677 | B1 * | 1/2007 | Bendall et al. .................. 359/464 |
| 7,347,817 | B2 | 3/2008 | Glukhovsky et al. |
| 2001/0017649 | A1 | 8/2001 | Yaron |
| 2001/0025135 | A1 | 9/2001 | Naito et al. |
| 2001/0035902 | A1 * | 11/2001 | Iddan et al. .................. 348/76 |
| 2001/0051766 | A1 | 12/2001 | Gazdzinski |
| 2002/0015952 | A1 | 2/2002 | Anderson et al. |
| 2002/0103417 | A1 * | 8/2002 | Gazdzinski .................. 600/109 |
| 2002/0109774 | A1 * | 8/2002 | Meron et al. .................. 348/74 |
| 2002/0146368 | A1 | 10/2002 | Meron et al. |
| 2002/0158976 | A1 | 10/2002 | Vni et al. |
| 2002/0173718 | A1 | 11/2002 | Frisch et al. |
| 2002/0177779 | A1 | 11/2002 | Adler et al. |
| 2003/0018280 | A1 | 1/2003 | Lewkowicz et al. |
| 2003/0020810 | A1 | 1/2003 | Takizawa et al. |
| 2003/0023150 | A1 | 1/2003 | Yokoi et al. |
| 2003/0028078 | A1 | 2/2003 | Glukhovsky |
| 2003/0045790 | A1 | 3/2003 | Lewkowicz et al. |
| 2003/0114742 | A1 | 6/2003 | Lewkowicz et al. |
| 2003/0130562 | A1 * | 7/2003 | Barbato et al. .................. 600/109 |
| 2003/0167000 | A1 | 9/2003 | Mulick et al. |
| 2003/0171648 | A1 | 9/2003 | Yokoi et al. |
| 2003/0171649 | A1 | 9/2003 | Yokoi et al. |
| 2003/0171652 | A1 | 9/2003 | Yokoi et al. |
| 2003/0195415 | A1 | 10/2003 | Iddan |
| 2003/0208107 | A1 | 11/2003 | Refael |
| 2003/0214579 | A1 | 11/2003 | Iddan |
| 2003/0214580 | A1 | 11/2003 | Iddan |
| 2003/0216622 | A1 | 11/2003 | Meron et al. |
| 2003/0227547 | A1 | 12/2003 | Iddan |
| 2004/0027459 | A1 | 2/2004 | Segawa et al. |
| 2005/0124858 | A1 | 6/2005 | Matsuzawa et al. |
| 2006/0264709 | A1 | 11/2006 | Fujimori et al. |
| 2006/0287580 | A1 | 12/2006 | Jo et al. |
| 2007/0167834 | A1 | 7/2007 | Pascal et al. |
| 2007/0191683 | A1 | 8/2007 | Fujimori |
| 2007/0232852 | A1 | 10/2007 | Pascal et al. |

FOREIGN PATENT DOCUMENTS

| | | |
|---|---|---|
| DE | 34 40 177 | 5/1986 |
| EP | 0 677 272 | 10/1995 |
| EP | 1 263 055 | 12/2002 |
| FR | 2688997 | 10/1993 |
| IL | 126727 | 10/1998 |
| IL | 143258 | 5/2001 |
| IL | 143259 | 5/2001 |
| JP | 5745833 | 3/1982 |
| JP | 4109927 | 4/1992 |
| JP | 4144533 | 5/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | H07-289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001-137182 * | 5/2001 |
| JP | 200122455 | 8/2001 |
| JP | 2001224551 | 8/2001 |
| JP | 2001231744 | 8/2001 |
| JP | 2001245844 | 9/2001 |
| JP | 2000342524 | 6/2002 |
| JP | 2000342525 | 6/2002 |
| JP | 2002010990 | 11/2002 |
| WO | WO 99/32028 | 7/1999 |
| WO | WO 00/76391 | 12/2000 |
| WO | WO 01/08548 | 2/2001 |
| WO | WO 01/10291 | 2/2001 |
| WO | WO 01/50941 | 7/2001 |
| WO | WO 01/65995 | 9/2001 |
| WO | WO 01/69212 | 9/2001 |
| WO | WO 02/054932 | 7/2002 |
| WO | WO 02/055984 | 7/2002 |
| WO | WO 02/067593 | 8/2002 |
| WO | WO 02/094337 | 11/2002 |
| WO | WO 03/003706 | 1/2003 |
| WO | WO 03/011103 | 2/2003 |
| WO | WO 2004/028336 | 4/2004 |
| WO | WO 2004/035106 | 4/2004 |

OTHER PUBLICATIONS

Robots for the future—Shin-ichi, et al., Nov. 2001.

The Radio Pill, Rowlands, et al., British Communications and Electronics, Aug. 1960, pp. 598-601.

Video Camera to "TAKE"—RF System Lab, Dec. 25, 2001.

Wellesley company sends body montiors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

BBC News Online—Pill camera to 'broadcast from the gut', Feb. 21, 2000, www.news.bbc.co.uk.
U.S. Appl. No. 12/172,422, filed Jul. 14, 2008, Gilad et al.
U.S. Appl. No. 09/807,892, filed Jun. 6, 2001, Meron et al.
U.S. Appl. No. 10/166,025, filed Jun. 11, 2002, Leckowicz et al.
U.S. Appl. No. 10/213,345, filed Aug. 7, 2002, Glukhovsky.
U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 60/297,761, filed Jun. 14, 2001, Lewkowicz et al.
U.S. Appl. No. 60/379,735, filed May 14, 2002, Iddan.
U.S. Appl. No. 60/379,752, filed May 14, 2002, Iddan.
U.S. Appl. No. 60/414,338, filed Sep. 30, 2002, Iddan.
Office Action of U.S. Appl. No. 11/645,787 mailed on Mar. 30, 2009.
Bio-Medical Telemetry: Sensing and Transmitting Biological Information from Animals and Man, R. Stuart Mckay, John Wiley and Sons, New York, 1970, pp. 244-245.
Evaluation of the heidelberg pH capsule: Method of Tubeless Gastric Analysis, Yarbrough, III et al., The American Journal Of Surgery, vol. 117, Feb. 1969, pp. 185-192.
Heidelberger Kapsel—ein Kleinstsender fur die pH-Messung im Magen, Lange, et al., Telefunken-Zeitung, Jg 36 (1963) Heft 5, pp. 265-270.
"In Pursuit of the Ultimate Lamp", Craford et al., Scientific American, Feb. 2001.
International Search Report of PCT/IL02/00391, dated May 19, 2003.
International Search Report for PCT/IL99/0554 dated Apr. 4, 2000.
Katgraber F, Glenewinkel F, Fischler S, Int J. Legal Med 1998; 111(3) 154-6.
Manual of Photogrammetry, Thompson (Ed.), Third Edition, vol. Two, Copyright 1944, 1952, 1966 by the American Society of Photogrammetry.
"New Smart Plastic has Good Memory"—Turke, European Medical Device Manufacturer, devicelink.com.
wwvv.pedinc.com Personal electronic devices, © 1997.
Supplementary Partial European Search Report, Mar. 9, 2004.
"The Heidelburg pH Capsule System Telemetric Fasting Gastric Analysis", Heidelburg International. Incorporated.
Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.
www.jason.net/tinycam.htm, © 2001, printed Dec. 19, 2001.
www.middleeasthealthmag.com/article2.htm—Review proves the value of computers, © 2001, printed Nov. 29, 2001.
International Search Report of Application No. PCT/IL07/01553 issued on Jun. 24, 2008.
Office Action of U.S. Appl. No. 11/645,787 mailed on Jun. 18, 2008.
US Office Action issued for U.S. Appl. No. 11/645,787, dated Aug. 12, 2009.
JP Office Action issued for application No. 2003-335881, dated Sep. 8, 2009.

* cited by examiner

OPTICAL HEAD ASSEMBLY WITH DOME, AND DEVICE FOR USE THEREOF

PRIOR PROVISIONAL APPLICATIONS

The present invention claims the benefit of prior U.S. provisional application Ser. No. 60/379,752, filed 14 May 2002, entitled "OPTICAL HEAD ASSEMBLY WITH AN OPTICAL DOME", and of prior U.S. provisional application Ser. No. 60/379,735, filed 14 May 2002, entitled "OPTICAL HEAD ASSEMBLY WITH AN OPTICAL DOME", and of prior U.S. provisional application Ser. No. 60/414,338, filed 30 Sep. 2002, entitled "MULTI-SECTIONAL OPTICAL DOME AND OPTICAL HEAD ASSEMBLY", each of which are incorporated by reference herein.

FIELD OF THE INVENTION

The present invention relates generally to optical head assemblies, and more specifically to optical head assemblies for in vivo imaging devices.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities. Generally, these devices perform in-vivo imaging using an imager such as an imaging sensor array (e.g., a CMOS camera, although other types of imagers may be used) and an internal light source, such as for example a "white LED" or any other suitable light source, which supplies the light for illuminating the area which needs to be imaged. Light is reflected from the surface illuminated by the light source and an optical system focuses the reflected light onto the CMOS imaging sensor.

The optical system may include one or more optical elements, such as one or more lenses, one or more composite lens assemblies, one or more suitable optical filters, or any other suitable optical elements adapted for focusing an image on the imaging sensor and for manipulating light as is known in the art. The optical system may be attached to, or mounted on, or fabricated on or disposed adjacent to the imager light sensitive CMOS as is known in the art. The optical system and CMOS imaging sensor are typically accurately aligned to obtain proper focusing and optical use of the CMOS surface area. The small scale of parts makes it difficult to obtain proper alignment.

The combination of the light source, imaging array (e.g. CMOS) and optical focusing system may be referred to as an optical head. The optical head is commonly placed behind an optical window or dome to, for example, isolate its electric components from liquids found in a body, which may interfere with the operation of these components. For these optical systems it is advantageous to have the illuminating element and receiving means contained within a single compartment. Having a single optical window is advisable for hygienic and practical considerations as well.

A system having the illumination element and means for receiving reflected light contained behind a single optical window or dome may have back-scatter and stray light produced by light remitted from the optical window itself received by the receiving means.

There is therefore a need for a system having illumination elements and means for receiving reflected light behind a single optical window in which proper alignment is easily achieved and in which backscattered light is reduced.

SUMMARY OF THE INEVNTION

According to some embodiments of the present inventions there is provided a system containing at least one illumination portion and at least one imaging portion behind a single dome with reduced adverse effects do to back-scatter and stray light and with improved alignment between image sensor and lens system.

According to some embodiments the dome has an optical system integrated therein.

According to other embodiments the dome is made of one or more materials and/or may be a multi sectional dome. The dome may be a combination of more than one material.

According to other embodiments the system has an alignment element integrated to the imaging portion and/or to the dome. The alignment element may be, for example, a shim, a cone, a shoulder, a lens holder, a ring or one or more positioning grooves, or other structures.

According to other embodiments the system has an optical isolation element integrated, typically in the imaging portion.

BRIEF DESCRIPTION OF THE DRAWINGS

The invention is herein described, by way of example only, with reference to the accompanying drawings, in which like components are designated by like reference numerals, wherein.

Figure 1:
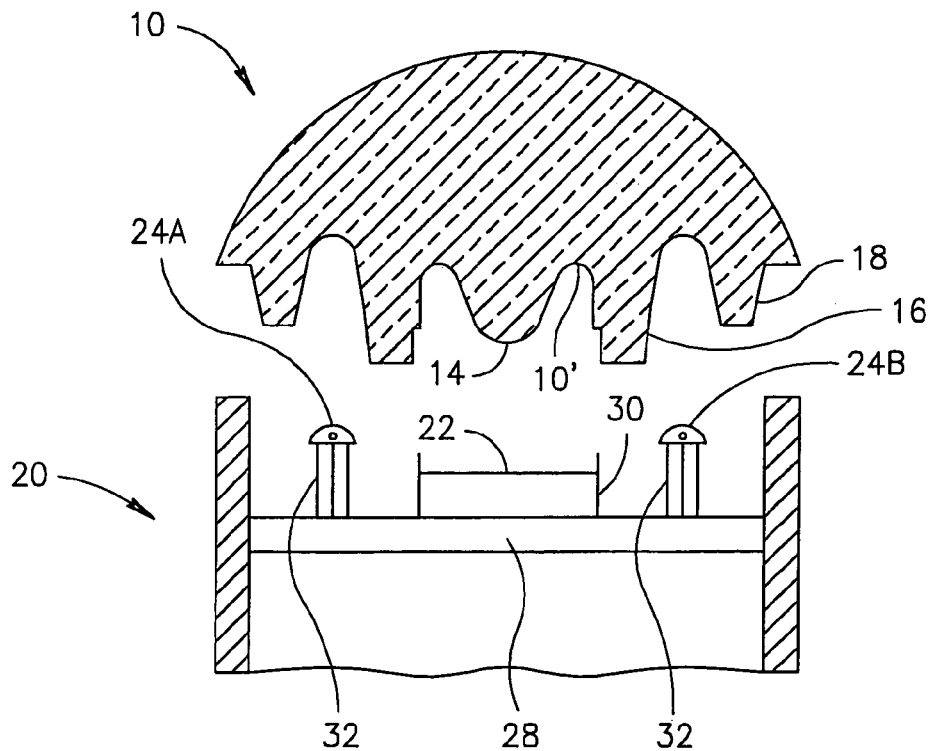
FIG. 1 illustrates an optical head assembly with a solid dome, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

An optical head assembly with dome may be utilized for in vivo imaging. For example, an optical head according to an embodiment of the invention can be incorporated in an in vivo device, such as a swallowable capsule for imaging the gastrointestinal (GI) tract, an endoscope, a catheter, a stent, a needle and others. In a device where a portion of the device is inserted, typically, an optical head, according to an embodiment of the invention, is incorporated or attached onto the distal end (the end which is inserted into a patient's body) of an in vivo device. In one embodiment the optical head is incorporated into a swallowable imaging capsule, such as, for example, the capsule described in WO 01/65995 and/or in U.S. Pat. No. 5,604,531 to Iddan, which are assigned to the common assignee of the present invention and which are hereby incorporated by reference.

Throughout the discussion of the invention some elements may be referred to as being "optical", or as being adapted to generate, receive, translate, or the like, optical radiation, however it should be understood that some embodiments of the present invention may include equivalent elements that may be adapted to generate, receive, translate, or the like, other forms of energy (e.g., infra red energy), typically energies that may be suitable for imaging the body lumen, and that such non-optical elements may be combined with, or replace, the optical elements.

Reference is now made to FIG. 1 that schematically illustrates an optical head assembly with a dome, according to an embodiment of the invention. Dome 10 is a solid dome including an integrated optical system 14 and, optionally, alignment elements, for example, shoulders 16 and 18 for positioning dome 10 onto optical head 20 during assembly. Alignment elements may include opaque material. According to one embodiment the alignment element(s) may be integral to the dome, (e.g., shoulders 16 and 18) optionally being made of the same material the as the dome. According to other embodiments, other alignment means, e.g. shims or other structures may be used or such means need not be used. According to one embodiment optical system 14 may include at least a lens. According to other embodiments optical system 14 may include one or more mirrors, prisms, composite lenses or any other suitable focusing and/or light directing elements. According to one embodiment the optical system 14 is positioned substantially near the inner surface 10' of the dome 10. Optical head 20 includes for example, an imager such as an image sensor 22, optical isolation element 30, and one or more light sources 24A and 24B mounted on a supporting means, for example a printed circuit board ("PCB") 28. Other supporting means may be used. Further, other components or combinations of components may be used.

Dome 10 may be made from, for example, translucent or partially translucent material. Dome 10 may be made from, for example, PMMA, isoplast™ (poly urethane), Cyclic Olefin Polymer (COP), Cyclic Olefin Copolymer (COC), polycarbonate, a copolymer of 70% polystyrene and 30% acrylic, having a refractive index at 588 nm of 1.564 (NAS) (other proportions and properties may be used) or any other suitable plastic, polymer, or material known in the art. The dome 10 is typically used to, for example, isolate or protect electric or other components from liquids found in a body, and to protect the optical head 20 from an in-vivo or other external environment. Other or additional functionality may be attached to the dome 10.

Image sensor 22 may include a single element or multiple elements, for example image sensor 22 may include an array of individual image sensors, and each of the independent image sensors may be adapted to operate cooperatively with each other image sensor. The individual image sensors may also be adapted to operate independently. Image sensor 22 may be a CMOS, a charge couple device ("CCD"), Indium Galium Arsenide (InGaAs), or any other suitable device.

Optical isolation element 30, may be, for example, made from an opaque or translucent barrier, a light trap, an optical filter, a series of separate barriers, or any other suitable structure of any suitable material, such as for example opaque plastic. Optical isolation element 30 may extend directly from the image sensor 22 or from PCB 28. An optical filter (not shown) such as for example an IR reject filter may be placed in the device, for example, between the image sensor 22 and the optical system 14. The illumination portion may include suitable illumination sources such as color LEDs, laser diodes or white LEDs. In an embodiment of the present invention, the light sources may have optical filters, such as IR reject filters, color filters, or other filters. One or more optical filters may be placed over one or more of the light sources. According to other embodiments a filter need not be included.

In one embodiment of the invention, solid dome 10 with one or more shoulders for example shoulders 16 and/or shoulder 18 provide a guide for aligning the image sensor 22 with optical system 14 integrated onto solid dome 10. As such, optimal use of the surface of the image sensor can be obtained. One or more light sources, such as 24A and/or 24B may be positioned between shoulders 16 and 18 respectively for optimal lighting of a target object to be imaged (not shown). Light sources 24A and 24B may be mounted on PCB 28 with, for example, flexible connectors 32 so that light sources 24A and 24B can be properly positioned between one or more shoulders 16 and 18 during assembly of the dome 10 with optical head 20. Other mounting methods may be used. In another embodiment (not shown) one or more light sources 24A and 24B are rigidly mounted on more than one PCB, for example, and alignment of image sensor 22 and light sources 24A and 24B between the shoulders 16 and 18 for example is accomplished by adjusting the relative position between the PCBs.

One or more light sources 24A and 24B radiate outward through the integrated dome toward an object (not shown) from which the light is reflected. Light rays reflected from a target object are focused with optical system 14 on to image sensor 22. Solid dome 10, which essentially surrounds the light sources 24A and 24B with dome material, may avoid the backscatter occurring due to rays from the light source hitting an inner surface of a shelled dome by eliminating the common inner surface that exists in a shelled dome. Optical isolation element 30 isolates image sensor 22 from stray light originating from light sources 24A and 24B.

In another embodiment of the invention, the inner and/or outer wall of shoulder 16 may be covered with an opaque material (not shown) so as to, for example, provide an isolating well for image sensor 22 and integrated optical system 14 against stray and back scattered light originating from one or more light sources 24A or 24B.

Figure 2A:
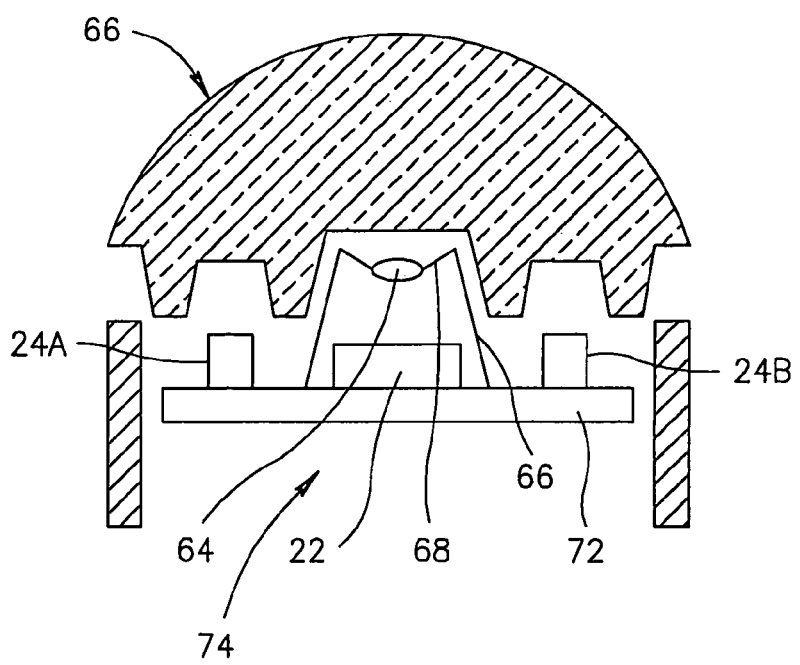
FIG. 2A schematically illustrates a solid dome with an optical head assembly, according to another embodiment of the present invention.

Reference is now made to FIG. 2A that schematically illustrates a solid dome 66 with an optical head assembly 74, according to one embodiment of the present invention. Optical head assembly 74 includes for example, image sensor 22, lens holder 66 with lens system 64, and one or more light sources 24A and 24B mounted on a support means, for example PCB 72. Image sensor 22 may be a CMOS, a CCD or any functional equivalent. Lens holder 66 fixes lens system 64 in a fixed position relative to the image sensor 22 so that, for example, optimal use of image sensor surface may be accomplished. Lens holder 66 may be, for example, an extension from image sensor 22 or an extension from PCB 74. Alternately, lens holder 66 may be separately added or may extend from another structure. According to one embodiment lens holder 66 with integrated well 68 may be, for example, made from an opaque or translucent barrier, a light trap, an optical filter, a series of separate barriers, or any other suitable structure of any suitable material such as for example opaque plastic. Lens holder 66 may as such provide a dual purpose of aligning lens system 64 with image sensor 22 and blocking out stray light or back scatter originating from the light sources 24A and 24B. In one embodiment of the invention, dome 66 may be, for example, an ellipsoid shaped dome or any other shape having at least one focal curve, for example, as is described in WO 00/76391, which is assigned to the common assignee of the present invention and which is hereby incorporated by reference in its entirety. Other suitable shapes, such as shapes not shown in the figures, may of course be used.

Figure 2B:
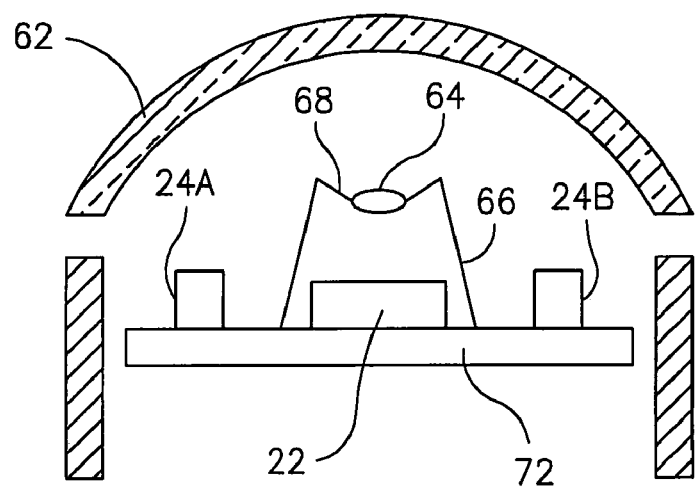
FIG. 2B schematically illustrates a shelled dome with an optical head assembly, according to one embodiment of the present invention.

FIG. 2B schematically illustrates an embodiment with a shelled dome 62 assembled with an optical head similar to that shown in FIG. 2A. In one embodiment of the invention, dome 62 may be for example an ellipsoid shaped dome or any other shape having at least one focal curve, for example, as is described above. One or more light sources 24A and 24B may be positioned in the focal curve while the image sensor array may be placed on the axis of symmetry. As such, when illuminating, rays from the light sources that are internally reflected from the dome inner surfaces, are not incident on the receiving means, for example image sensor 22. Lens holder 66 with well 64 isolate the lens system that is set at a height above the image sensor from stray and backscattered light originating from the one or more light sources 24A and 24B.

Figure 3:
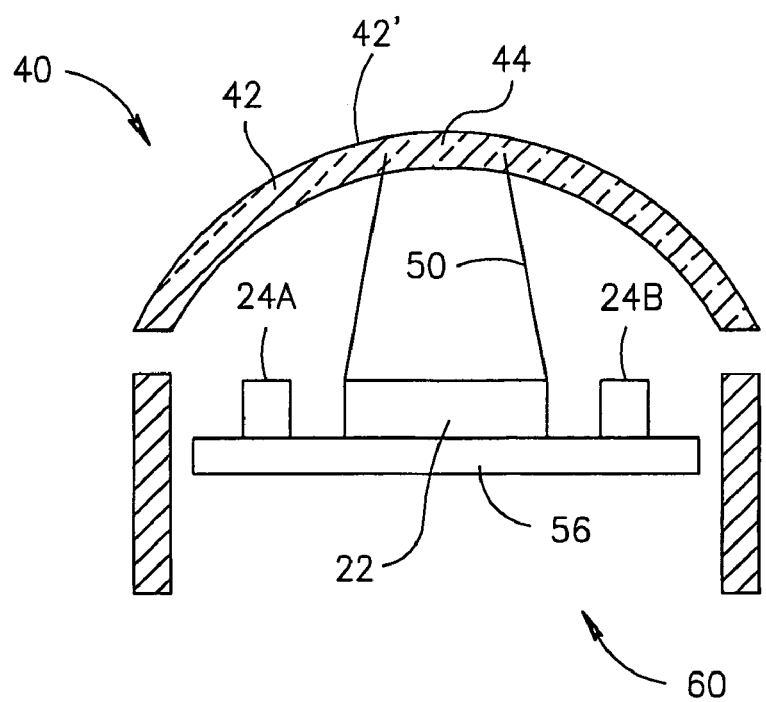
FIG. 3 schematically illustrates a shelled dome with an optical head assembly, according to another embodiment of the present invention.

Reference is now made to FIG. 3 that schematically illustrates a system which includes an optical head assembly with a dome, according to another embodiment of the invention. System 40 includes a shelled dome 42 integrated with optical system 44 and an optical head 60. Optical head 60 includes image sensor 22 and one or more light sources 24A and 24B mounted on a support means, for example PCB 56. According to one embodiment optical isolation element 50 may extend from PCB 56, surrounding the image sensor 22, to dome 42 and is fixed, at its upper end, against dome 42. In another embodiment, the optical isolation elements may be, for example, extensions of the light elements or image sensors (or other components), or a piece integrated into the dome or lens. The optical isolation element 50 may be, for example, an opaque or translucent barrier, a light trap, an optical filter, a series of separate barriers, or any other suitable structure of any suitable material such as for example opaque plastic. According to one embodiment optical isolation barrier 50 which may have a ring shaped bottom end, may be mounted within the dome 42 structure by, for example, gluing, acoustic welding, friction fit, being held by other assembled components, or by other methods. The bottom end of the ring may be fixed directly to PCB board 56 using any suitable methods known in the art. During assembly of dome 42 to optical head 60, the ring of isolation element 50 insures that optical lens 44 is properly aligned to image sensor 22. Isolation element 50 also serves to isolate image sensor 22 from stray light originating from the light source, e.g., 24A and/or 24B. In this embodiment, dome 42 does not need to have any specific geometrical shape including shapes with focal curves since the optical system 44 is integrated substantially near the outer surface 42' of the dome and therefore does not receive backscattered light. Stray light may be avoided with an opaque isolation element 50. In one embodiment, if a device, such as a capsule, in which the isolation element 50 is used is, for example, 11 mm in diameter, the isolation element 50 can have a thickness of, for example, less than 1 mm. Other dimensions can be used.

Figure 4A:
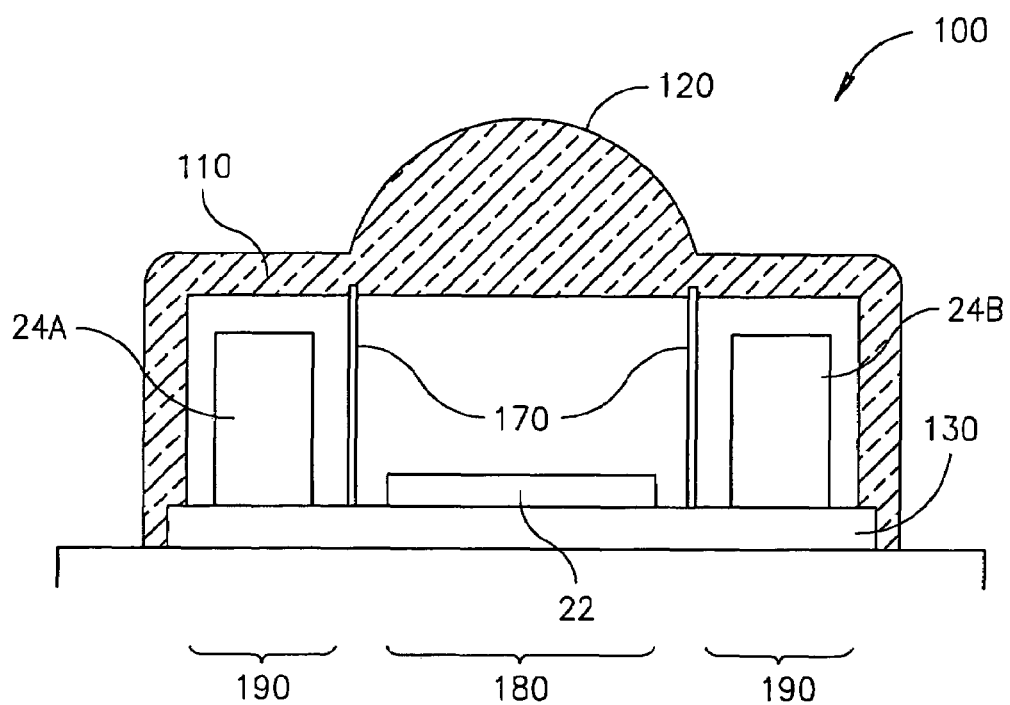
FIG. 4A schematically illustrates a cross sectional view of an optical head assembly with a multi-sectional dome according to an embodiment of the present invention.

Turning to FIG. 4A, there is shown a schematic cross sectional view of an optical head assembly with a multi-sectional dome 100 according to an embodiment of the present invention. According the embodiment shown in FIG. 4A, an optical lens 120 may be integrated into a dome 110. One or more of the illumination elements such as illumination elements 24A and 24B provide illumination and one or more image sensors 22 capture images. The area generally beneath the lens 120 may form one section, the imaging section 180, of the dome 110, while the other area or areas, generally not beneath the optical lens 120 and generally associated with illumination elements 24A and 24B, may form one or more illumination sections 190 of the dome 110.

One or more optical isolation elements 170 may be used to separate at least one illumination section 190 and imaging section 180. In FIG. 4A isolation element 170 is shown as a cross section of a single ring, but it may have other suitable forms such as for example cone shaped. Isolation element 170 may be part of or an extension of other elements, such as PCB 130 or any support surface such as a silicon surface. Isolation element 170 may be mounted within the structure 110 by, for example, gluing, acoustic welding, friction fit, being held by other assembled components, or by other methods. Isolation element 170 in this case also helps to isolate image sensor 22 from backscatter as well as allowing controlled alignment between lens 120 and image sensor 22. In other embodiments, other numbers of optical isolation elements may be used, having different forms. The optical isolation elements may be, for example, extensions of the light elements or imagers, a piece integrated into the dome or lens, a translucent or semi-transparent member, or other suitable forms.

Generally, an illumination section includes the area including illumination elements and an imaging section includes areas including one or more imagers. However, an illumination section may include other components and areas, and an imaging section may include other components and areas. Further, each of an illumination section and imaging section may be divided into two or more non-contiguous sections, and may have different configurations than shown. For example, several illumination sections may exist as "islands" within an overall imaging section, or each of an illumination section(s) and an imaging section(s) may in turn be located within another area. Furthermore, illumination section(s) and an imaging section(s) need not be completely divided—e.g., the optical isolation element(s) may not completely divide the sections, may include holes, may be translucent, etc.

In one embodiment of the present invention, as exemplified in FIG. 4A, one or more of the illumination elements 24A or 24B and one or more image sensors 22 may be situated on a support surface 130 such as a PCB; the support surface 130 may be components other than a circuit board. In alternative embodiments, one or more of the illumination elements 24A or 24B and one or more image sensors 22 may be situated on separate support surfaces 130, on a common silicon substrate, or on another structure, and need not be mounted on or fastened to the same structure.

Figure 4B:
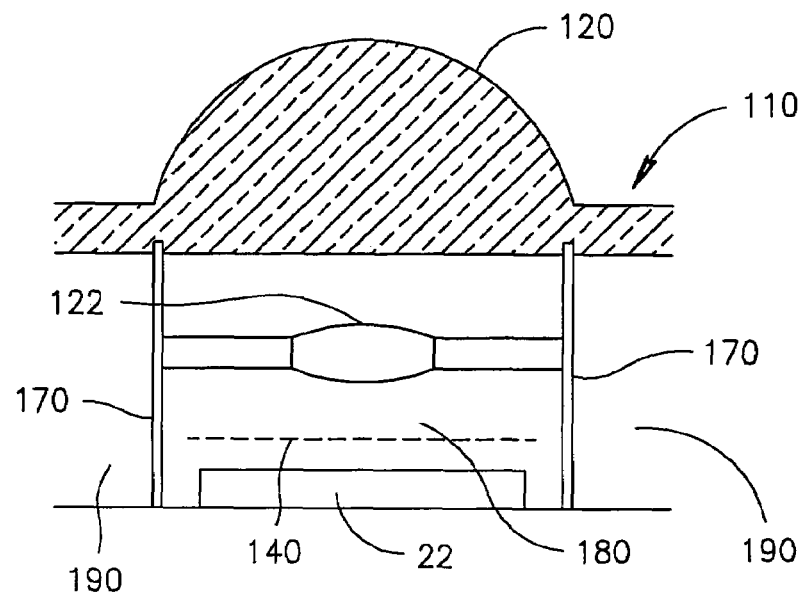
FIG. 4B schematically illustrates a cross sectional view of the imaging portion of an optical head assembly with multi-sectional dome according to an embodiment of the present invention.

Reference is made now to FIG. 4B, which is a schematic cross sectional view of the imaging portion of an optical head assembly with multi-sectional dome according to an embodiment of the present invention. In the embodiment shown, the imaging portion may include an inner lens 122, either in addition or in alternative to lens 120. The inner lens 122 may be placed within the dome 110 in a position relative to the image sensor 22, such that the inner lens 122 may be capable of focusing inbound light onto the image sensor either independently or jointly in case that the dome 110 includes a lens 120 fixed thereto.

An optical filter 140 may be placed between the image sensor 22 and the lenses 120 and/or 122. An optical filter 140 may also be placed in other locations. According to some embodiments of the present invention one or more illuminating elements 24A or 24B (e.g., in FIG. 4A) provide illumination from an illumination section 190 of the multi-sectional dome 110. The illuminating elements 24A and 24B may produce a light which radiates outward through the dome 110 towards an object from which the light may be reflected. The reflected light may then be received by the imaging portion by entering through the lens 120. Other illuminating elements may be used.

Figure 5:
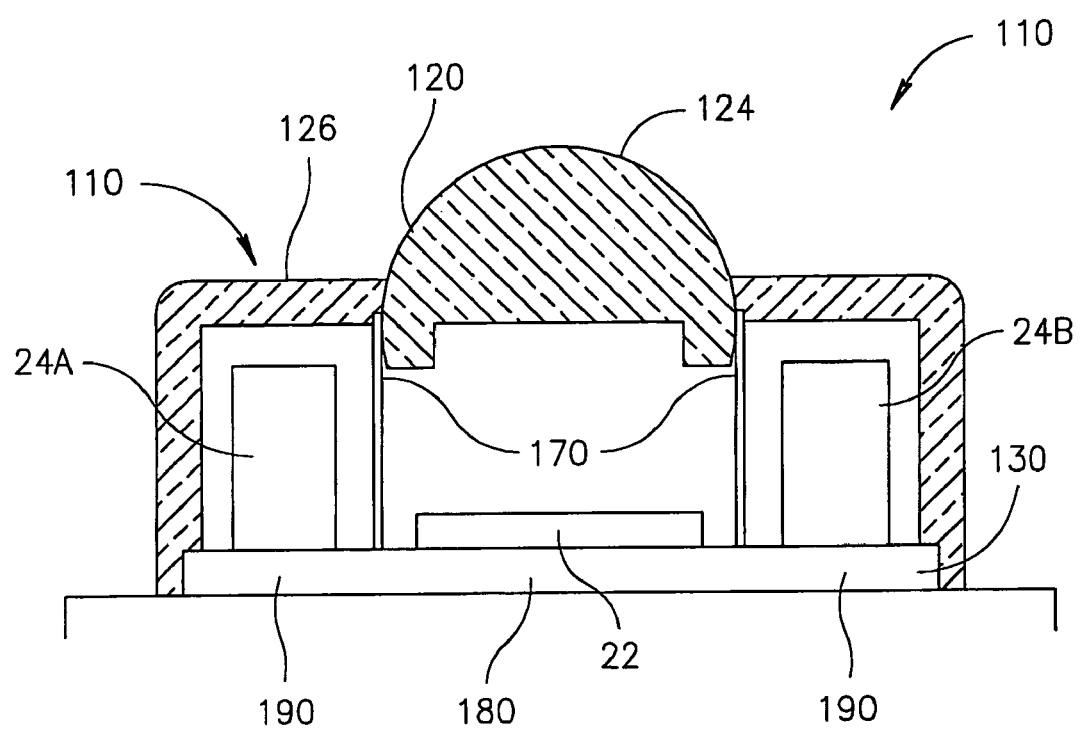
FIG. 5 schematically illustrates a cross sectional view of an optical head assembly with non-homogenous multi-sectional dome according to an embodiment of the present invention.

Reference is made now to FIG. 5, which is a schematic cross sectional view of an optical head assembly within a system according to an embodiment of the present invention. According to one embodiment the system includes a multi sectional dome 110 and an optical head assembly. Multi-sectional dome 110 may be non-homogenous. For example dome 110 may include two or more separable portions or sections, e.g., an imaging dome portion 124 and an illumination dome portion 126. The imaging dome portion 124 may include a lens 120 integrated thereto. One or more illumination elements 24A and 24B and one or more image sensors 22 are included in the optical head assembly. The lens 120 may be placed in a position relative to the image sensor 22 and have such optical characteristics such that the lens 120 may focus inbound light onto the image sensor 22. One or more optical isolation elements 170 may be used to separate sections of the multi-sectional dome 110. Multi-sectional dome 110 and optical isolation element 170 may be assembled by gluing, laser welding, ultrasonic welding, or any other suitable method. Components may be mounted on a support surface 130 such as a PCB. The one section, e.g., the section which includes the lens 120 may be positioned above the imaging section 180 whereas another section may be positioned above the illumination section(s) 190.

Figure 6:
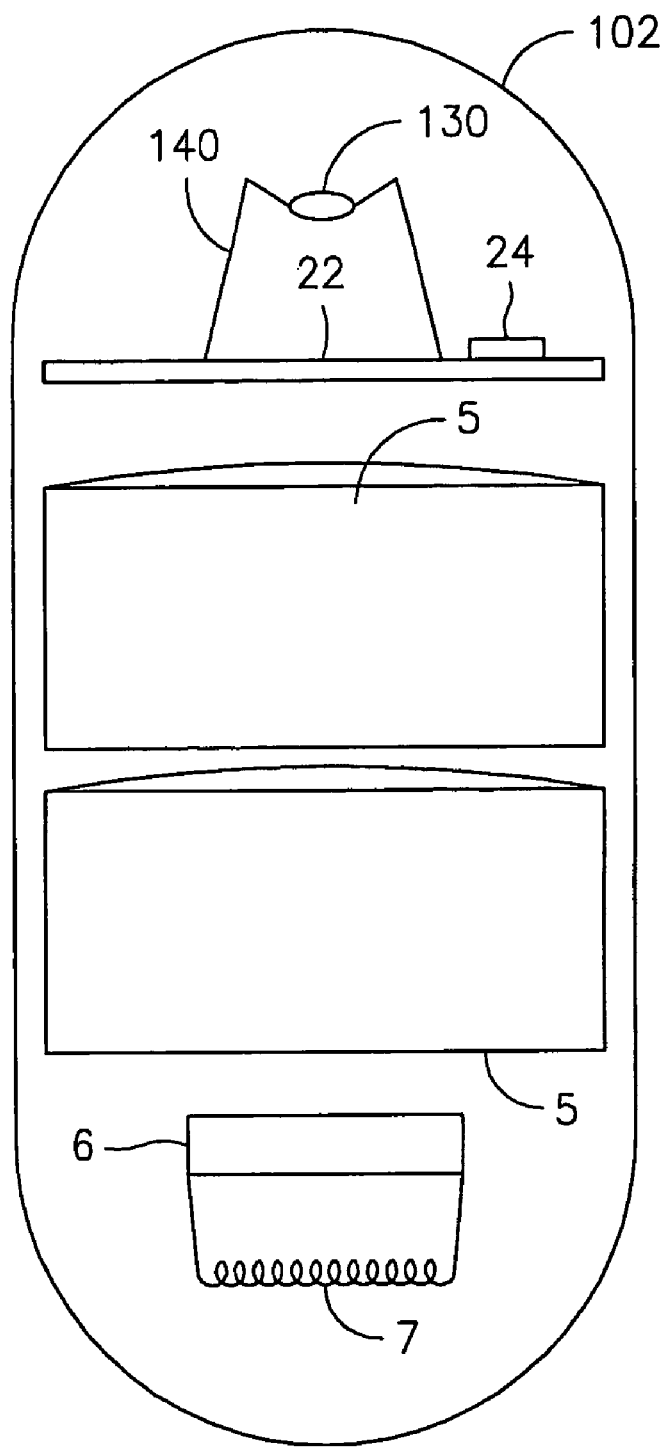
FIG. 6 schematically illustrates an in vivo imaging device with an optical head and dome, according to an embodiment of the invention.

Turning now to FIG. 6, there is shown an in vivo imaging capsule with an optical head and dome, according to an embodiment of the invention. The diagram in FIG. 6 illustrates a possible general arrangement of an optical head and dome according to the present invention relative to other components within an in vivo capsule. The dome 102 according to embodiments of the invention and the optical head; having illuminating elements 24, a lens 130 on lens holder 140 and an image sensor 22, may be positioned on an end of a cylindrical capsule having batteries 5, a transmitter 6, and an antenna 7. Other arrangements of components may be used in accordance with embodiments of the current invention. For example, an optical head according to an embodiment of the invention may be located along side the long axis of an in vivo capsule. The in vivo capsule can be operated similarly to known in vivo capsules, for example, the capsule described in the above mentioned WO 01/65995 and/or U.S. Pat. No. 5,604,531 to Iddan. In another embodiment the capsule need not comprise a contained power source, such as a battery, but may be, for example, externally powered. Alternatively, an optical head according to an embodiment of the invention may be located at the inserted end of other in vivo devices, such as, endoscopes, stents, needles, catheters etc.

While the invention has been described with respect to a limited number of embodiments, it will be appreciated that many variations, modifications and other applications of the invention may be made which are within the scope and spirit of the invention.

The invention claimed is:

1. A system comprising:
a single optical head assembly; and
a multi-sectional shelled dome to cover said optical head assembly, wherein the single optical head assembly comprises:
an illumination portion; and
an imaging portion,
the illumination portion comprising an illumination source and the imaging portion comprising an image sensor and a lens, wherein said illumination portion and said imaging portion face the same direction,
the multi-sectional shelled dome comprising:
an imaging dome portion to receive light reflected from an external object; and
an illumination dome portion distinct from said imaging dome portion to enable radiation of light towards the external object, and
wherein the imaging dome portion comprises a convex surface and is located at the center of the dome and the illumination dome portion comprises a flat surface, the imaging dome portion extending from the dome beyond the flat surface of the illumination portion; and
wherein the dome is spaced from the illumination source and the image sensor and lens by a gap.

2. The system according to claim 1 comprising an optical isolation element.

3. The system according to claim 2 wherein the optical isolation element is situated between the illumination portion and the imaging portion.

4. The system according to claim 1, wherein the illumination portion comprises white LEDs, color LEDs, laser diodes or any combination thereof.

5. The system according to claim 1 comprising an optical system, wherein the optical system is selected from a group comprising one or more lenses, one or more composite lens assemblies, one or more optical filters, one or more mirrors, one or more prisms or combination thereof.

* * * * *